US010849994B2

(12) United States Patent
Llop Roig et al.

(10) Patent No.: US 10,849,994 B2
(45) Date of Patent: Dec. 1, 2020

(54) PHARMACEUTICAL COMPOSITION COMPRISING FLUORINE-18 LABELLED GASES

(71) Applicant: ASOCIACIÓN CENTRO DE INVESTIGACIÓN COOPERATIVA EN BIOMATERIALS—CIC BIOMAGUNE, San Sebastián (ES)

(72) Inventors: Jordi Llop Roig, San Sebastián (ES); Vanessa Gómez Vallejo, San Sebastián (ES); Torsten Reese, San Sebastián (ES); Aitor Lecuona Fernändez, San Sebastián (ES)

(73) Assignee: ASOCIACIÓN CENTRO DE INVESTIGACIÓN COOPERATIVA EN BIOMATERIALES — CIC BIOMAGUNE, San Sebastián (ES)

( * ) Notice: Subject to any disclaimer, the term of this patent is extended or adjusted under 35 U.S.C. 154(b) by 0 days.

(21) Appl. No.: 16/310,723

(22) PCT Filed: Jun. 27, 2017

(86) PCT No.: PCT/EP2017/065900
§ 371 (c)(1),
(2) Date: Dec. 17, 2018

(87) PCT Pub. No.: WO2018/022079
PCT Pub. Date: Jan. 4, 2018

(65) Prior Publication Data
US 2019/0262482 A1    Aug. 29, 2019

(30) Foreign Application Priority Data

Jun. 28, 2016 (EP) ..................... 16382304

(51) Int. Cl.
| | | |
|---|---|---|
| *A61K 51/12* | (2006.01) | |
| *A61K 51/04* | (2006.01) | |
| *A61K 51/02* | (2006.01) | |
| *C07B 59/00* | (2006.01) | |

(52) U.S. Cl.
CPC ........ *A61K 51/1206* (2013.01); *A61K 51/025* (2013.01); *A61K 51/04* (2013.01); *C07B 59/00* (2013.01)

(58) Field of Classification Search
CPC ......... A61K 51/02; A61K 51/04; A61K 51/12
See application file for complete search history.

(56) References Cited

U.S. PATENT DOCUMENTS

| | | | | |
|---|---|---|---|---|
| 8,231,855 B2* | 7/2012 | Omotowa | ............ | C01B 17/453 423/469 |
| 2005/0129162 A1* | 6/2005 | Ruth | ........................ | G21G 1/10 376/195 |

FOREIGN PATENT DOCUMENTS

DE    102005026253    1/2006

OTHER PUBLICATIONS

Richard M. Lambrecht et al. Cycloctron Isotopes and Radiopharmaceuticals—XXIIL, Novel Anhydrous 18F-Fluorinating Intermediates, Int. J. Applied Radiation and Isotopes, vol. 29, 175-183. (Year: 1978).*
E. Hess et al. Improved target system for production of high purity [18F]fluorine via the 18O(p,n) 18F reaction, Applied Radiation and Isotopes, 52, 1421-1440. (Year: 2000).*
International Search Report and Written Opinion dated Sep. 28, 2017 for PCT Application No. PCT/EP2017/065900, 18 pages.
Banister, Samuel, et al. "Fluorine-18 chemistry for PET: A concisde introduction", Current Radiopharmaceuticals Mar. 2010, vol. 2, No. 2, pp. 68-80.
Boggs, James E., et al, "Non-exchange of F18 between HF and Fluroinated Methanes", J. Am. Chem. Soc. Dec. 20, 1955, vol. 77, No. 24, pp. 6505-6506.
Cramer, John A., et al, "Gase phase fluorination of Benzene, Fluorobenzene, m-Difluorobenzene, and Trifluoromethylbenzene by Reactions of Thermal Fluorine—18 Atoms", J. Am. Chem. Soc. Oct. 1974, vol. 96, No. 21, pp. 6579-6584.
Gens, T.A., et al, "The exchange of F18 between metallilc fluorides and gaseous fluorine compounds", J. Am. Chem. Soc. Feb. 20, 1957, vol. 79, pp. 1001-1002.
Gomez-Vallejo, V., et al. "Ion beam induced 18F—radiofluorination straightforward synthesis of gaseous radiotracers for the assessment of regional lung ventilation using positron emission tomography", Chem Comm. Sep. 7, 2016, vol. 52, No. 80 pp. 11931-11934.
Hess, E., et al, "Improved target system for production of high purity [18F]fluorine via the 18O(p,n)18F reaction", Applied Radiation and Isotopes Jun. 1, 2000, vol. 52, No. 6, pp. 1431-1440.
Knickelbein, Mark B., et al, "Recoil, 18F Chemistry. XIII: High-pressure investigation of CF4", Chemical Physics Jan. 1, 1984, vol. 83, No. 1-2, pp. 235-245.
Lambrecht, Richard M., et al., "Cyclotron isotopes and radiopharmaceuticals—XXIII.* Novel Anhydrous 18F-Fluorinating Intermediates", International Journal of Applied Radiation and Isotopes Mar. 1, 1978, vol. 29, No. 3, pp. 175-183.
Murata, Kiyoshi MD., et al. "Ventilation imaging with positron emission tomography and Nitrogen 13-1", Radiology Feb. 1986, vol. 158, pp. 303-307.

(Continued)

*Primary Examiner* — Michael G. Hartley
*Assistant Examiner* — Jagadishwar R Samala
(74) *Attorney, Agent, or Firm* — Squire Patton Boggs (US) LLP

(57) ABSTRACT

There is provided a process for the preparation of a pharmaceutical composition comprising an $^{18}$F-labelled gas selected from the group consisting of $^{18}$F-labelled sulphur hexafluoride ([$^{18}$F]SF$_6$) and $^{18}$F-labelled carbon tetrafluoride ([$^{18}$F]CF$_4$), comprising the steps: a) Filling a target with a gas mixture comprising a fluorinated gas selected from the group consisting of sulphur hexafluoride (SF$_6$) and carbon tetrafluoride (CF$_4$); b) Irradiating the gas mixture of step a) with protons with energies from 0.1 to 50 MeV. The pharmaceutical composition obtainable by the process and its uses in diagnosis, prognosis and lung function studies based on positron emission tomography (PET) are also claimed.

8 Claims, 7 Drawing Sheets

(56) References Cited

OTHER PUBLICATIONS

Palmer, A.J., "Recoil labelling of Fluorine-18 labelled chlorofluoromethanes and tetrafluoromethane", International Journal of Applied Radiation and Isotopes Oct. 1, 1978, vol. 29, No. 9-10, pp. 545-548.
Rogers, Max. T., et al. "Fluorine exchange reactions between hydrogen fluoride and the halogen fluorides", J. Am. Chem. Soc. Mar. 20, 1952, vol. 74, pp. 1375-1377.
Smail, Thomas, et al., "Competitive addition of near-thermal fluorine-18 atoms to olefins", J. Am. Chem. Soc. Feb. 1, 1972, vol. 94, No. 4, pp. 1041-1046.
Scholz, Alexander-Wigbert, et al., "Comparison of magnetic resonance imaging of inhaled SF6 with respiratory gas analysis", Magnetic Resonance Imaging May 1, 2009, vol. 27, No. 4, pp. 549-556.
Williams, Ronald L., et al., "Reactions of Fluorine-18 atomrs with ethylene", Journal of Physical Chemistry Nov. 23, 1972, vol. 76, No. 24, pp. 3509-3517.
Yu, Jian-xin, et al., "19F: A versatile reporter for non-invasive physiology and pharmacology using magnetic resonance", Current Medicinal Chemistry 2005, vol. 12, No. 7, pp. 819-848.

* cited by examiner

PHARMACEUTICAL COMPOSITION COMPRISING FLUORINE-18 LABELLED GASES

This application claims the benefit of European Patent Application EP16382304.0 filed on Jun. 28, 2016.

The present invention provides a pharmaceutical composition comprising Fluorine-18 labelled gases for positron emission tomography (PET) and its method of preparation. The composition has applications in the field of diagnosis, prognosis and lung function studies of a wide range of respiratory diseases in different clinical settings.

BACKGROUND ART

Nuclear medicine is now a well-established field. It is based on the administration of radioactive molecules to a patient, and on the monitoring of the fate of those molecules inside the body. In nuclear medicine imaging, a radiopharmaceutical (a radio-labelled molecule) is administered by a variety of routes such as intravenously, orally or via ventilation, and then external detectors are used to capture and form images from the radiation emitted by the radiopharmaceutical once inside the body. This process is in contrast to diagnostics by X-ray, where external radiation is passed through the body to form an image. By monitoring via several different imaging technologies, the distribution, behavior and secretion of those molecules while inside the body can give a wealth of biochemical, metabolic and functional information that can be used for diagnostic purposes.

Among the most widely used imaging technologies, magnetic resonance imaging (MRI), X-ray computed tomography (CT), ultrasound imaging, and nuclear imaging techniques including Positron Emission Tomography (PET), Single Photon Emission Computerised Tomography (SPECT) and scintigraphy stand out. PET is based on the detection of pairs of gamma rays emitted indirectly by a positron-emitting tracer which is introduced into the body in the form of a variety of labelled molecules. The most commonly used label for PET applications is Fluorine-18 (Banister S., et al., "Fluorine-18 chemistry for PET: A concise Introduction "Current Radiopharmaceuticals 2010, vol. 3, pp. 68-80) although other labels such as Carbon-11, Nitrogen-13, Oxygen-15 or Copper-64, among others, have also been described. Three-dimensional images of tracer concentration within the body obtained by the scanner are then constructed by computer analysis. One of the most widely used PET tracers is currently $^{18}$F-Fluorodeoxyglucose (2-deoxy-2-($^{18}$F)fluoro-D-glucose or simply $^{18}$F-FDG), whose monitoring indicates high tissue metabolic activity as it corresponds to regions of high glucose uptake. This tracer is for instance used to diagnose cancer metastasis.

One of the areas for which PET is to be applied is in ventilation studies, enabling the diagnosis, prognosis and determination of response to treatment of a variety of pulmonary diseases, and in general the assessment of lung function. Currently, clinical ventilation studies to visualize local areas of impaired ventilation are mainly performed with Single Photon Emission Computerised Tomography (SPECT) or scintigraphy, not PET. However, PET offers much higher sensitivity and better spatial resolution than SPECT or scintigraphy, and enables absolute quantification. The fact that PET is not widely used in ventilation studies is mainly because of a series of limitations associated to the positron emitting labels.

Positron emitting-labelled gases for PET ventilation studies have been described based on Neon-19 or Nitrogen-13 labelled $N_2$ (see for instance Murata K., et al. "Ventilation imaging with positron emission tomography and Nitrogen-13" Radiology 1986, vol. 158, pp. 303-307). Unfortunately these isotopes are endowed with a very short half-life ($T_{1/2}$=17.4s and 9.97 min respectively) which impairs their widespread use and commercialization. Regarding SPECT, the contrast agents currently in use are particle-based; these produce hot spots in hypo-ventilated areas and remain in the lung for a long time, which might be a liability in terms of safety. Thus, there is a long felt need for new pharmaceutical compositions based on different radiotracers for PET ventilation studies with improved properties.

Bearing in mind that Fluorine-18 is one of the standard labels for PET applications and also considering that it has a much longer half-life than the isotopes cited above (109.7 mins) it could be argued that labelling different gases with Fluorine-18 could be the strategy of choice for ventilation PET diagnosis. However, a host of very serious limitations in the synthesis of Fluorine-18 labelled gases have so far made progress nearly impossible.

As can be seen in several nuclear magnetic resonance imaging disclosures, $SF_6$ is one of the most widely used gases for ventilation studies (see for instance Yu J, et al. "$^{19}$F: A versatile reporter for non-invasive physiology and pharmacology using magnetic resonance" Current Medicinal Chemistry 2005, vol. 12, pp. 819-848). The labelling of $SF_6$ with Fluorine-18 could enable the use of this gas for ventilation PET purposes. However, the production of such a labelled gas has been hindered for decades, already existing disclosures teaching away from its production dating as far back as the 1950's (see for instance Gens T. A. et al. "The exchange of F18 between metallic fluorides and gaseous fluorine compounds" J. Am. Chem. Soc. 1957, vol. 79, pp. 1001-1002, Rogers M. T., Katz J. "Fluorine Exchange reactions between hydrogen fluoride and the halogen fluorides" J. Am. Chem. Soc. 1952, vol. 74, pp. 1375-1377, Boggs et al: "Non-exchange of F18 between HF and Fluorinated Methanes", J. Am. Chem. Soc., 1955, 77 (24), pp 6505-6506, and Cramer et al: "Gas phase fluorination of benzene, fluorobenzene, m-difluorobenzene, and trifluoromethylbenzene by reactions of thermal fluorine-18 atoms", J. Am. Chem. Soc., 1974, 96 (21), pp 6579-6584). Thus, the development of new $^{18}$F-labelled gases for widespread PET applications has not made any real progress for a long time.

In view of the above, there is clearly a need for expanding the repertoire of gases for ventilation PET applications. Improved pharmaceutical compositions with convenient production processes comprising positron-emitting gases for use in PET would represent a step forward in this field of medicine.

SUMMARY OF THE INVENTION

Inventors have surprisingly devised a process to prepare a pharmaceutical composition comprising the $^{18}$F-labelled gases sulphur hexafluoride ($SF_6$) and carbon tetrafluoride ($CF_4$), such that the latter can be effectively administered to a subject to study lung function and for diagnostic, prognostic and patient stratification purposes. The efficiency of this process is unprecedented, enabling the convenient use of these two gases in Positron Emission Tomography (PET)-based ventilation diagnostic studies.

The pharmaceutical composition of the invention is endowed with a series of advantages when compared to what is available in the prior art, namely, a longer half-life which translates into a real applicability in the clinics. The pharmaceutical composition, comprising fluoride gases of the invention, has a lower solubility in water when compared to compositions based on other gases such as nitrogen or neon, a property that minimizes the chances for the gases to end up in the bloodstream when administered via inhalation for pulmonary diagnostic purposes. Therefore, the composition of the invention is both more effective and safer than the compositions described so far.

Thus, a first aspect of the invention is a process for the preparation of a pharmaceutical composition comprising an $^{18}$F-labelled gas selected from the group consisting of $^{18}$F-labelled sulphur hexafluoride (([$^{18}$F]SF$_6$) and $^{18}$F-labelled carbon tetrafluoride ([$^{18}$F]CF$_4$), comprising the steps: a) Filling a target with a gas mixture comprising a fluorinated gas selected from the group consisting of sulphur hexafluoride (SF$_6$) and carbon tetrafluoride (CF$_4$); b) Irradiating the gas mixture of step a) with protons with energies from 0.1 to 50 MeV;

A second aspect of the invention is a pharmaceutical composition comprising a pharmaceutically effective amount of an $^{18}$F-labelled gas selected from the group consisting of $^{18}$F-labelled sulphur hexafluoride (SF$_6$) and $^{18}$F-labelled carbon tetrafluoride (CF$_4$), and at least one pharmaceutically acceptable carrier.

A third aspect of the invention is a pharmaceutical composition according to the first aspect of the invention for use as an image contrast agent.

DETAILED DESCRIPTION OF THE INVENTION

Figure 1:
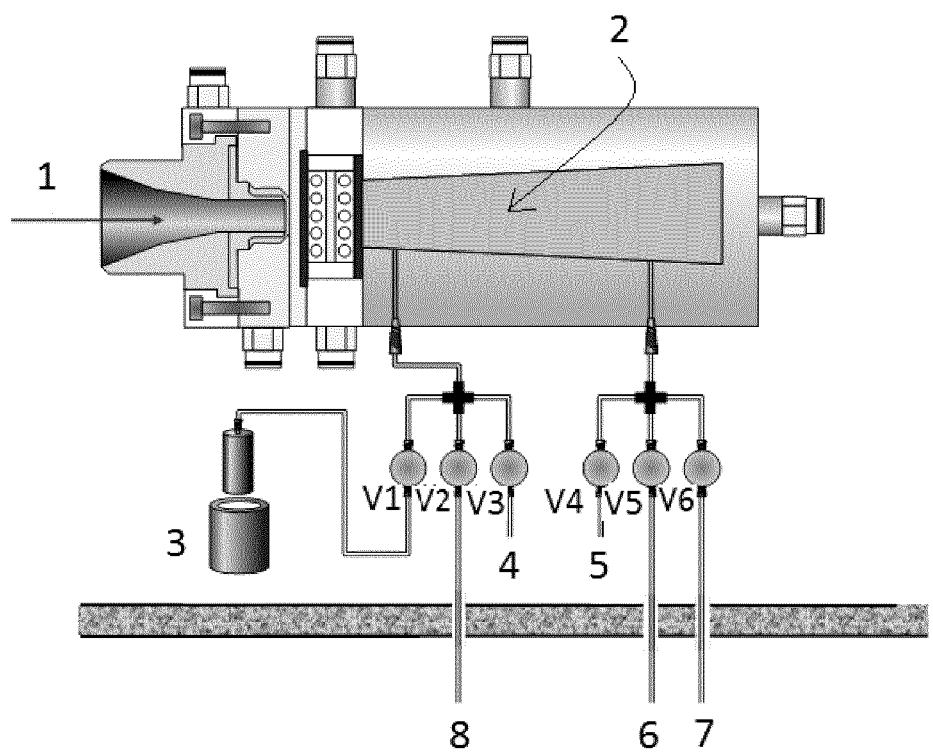
FIG. 1. Configuration of the target used for the production of [$^{18}$F]CF$_4$ and [$^{18}$F]SF$_6$; (1) proton beam; (2) target chamber; (3) stainless steel-high pressure container and liquid nitrogen cooling bath; (4) Exhaust; (5) [$^{18}$O]O$_2$ gas bottle; (6) Neon gas bottle; (7) CF$_4$ or SF$_6$ gas bottle; (8) radiochemistry lab; $V_1$-$V_6$ are 2-way, normally-closed electro-valves.

For the sake of understanding, the following definitions are included and expected to be applied throughout description, claims and drawings.

The term "pharmaceutical composition" refers to the mixture of $^{18}$F-labelled gases together with other components such as a carrier gas or a mixture of carrier gases or a diluent. The pharmaceutical composition facilitates the administration of $^{18}$F-labelled SF$_6$ or $^{18}$F-labelled CF$_4$ to the organism so that it can be traced inside the body by different imaging techniques in a precise and safe manner. Throughout this description, the terms "pharmaceutical composition" and "diagnostic composition" are considered equivalent and are used interchangeably. The administration of the "pharmaceutical composition" can be carried out for diagnostic, prognostic, patient stratification, response to treatment and other purposes. The "pharmaceutical composition" can be used in a diseased subject or in a normal subject, the subject being an animal including, but not limited to, a human. Thus, the "pharmaceutical composition" can also be a veterinary composition when given to a subject other than a human. Because the "pharmaceutical composition" in the context of the present invention comprises a radiolabelled gas, it could also be termed a "radiopharmaceutical composition".

The term "pharmaceutically effective amount" as used herein, refers to an amount of a compound (in this case $^{18}$F-labelled SF$_6$ or CF$_4$) which, when administered, is enough to enable imaging in an efficient, precise, reliable and yet safe manner, so that the image can aid in determining a diagnosis, prognosis, evolution of disease, patient stratification, lung function analyses, etc. It is to be noted that when administered via inhalation, any of the two gases (SF$_6$ or CF$_4$) are given as a mixture of $^{18}$F-labelled and $^{18}$F-unlabelled gas. The particular dose of gas administered according to the invention will be set obviously by the circumstances associated with each case, including the administered gas, the route of administration, the disease being diagnosed, the imaging technology used to interpret the emitted radiation, and similar considerations.

The term "pharmaceutically acceptable carrier" as used herein refers to pharmaceutically acceptable materials, compositions or excipients. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable risk/benefit ratio. In the present invention, the pharmaceutically acceptable carrier used for administering the $^{18}$F-labelled $CF_4$ or $SF_6$ can comprise air, water, nitrogen, oxygen, carbon dioxide, hydrogen, an inert gas, a sulphur fluoride, an optionally halogenated low molecular weight hydrocarbon, or a combination thereof.

For the purposes of the invention, the term "optionally halogenated low molecular weight hydrocarbon" encompasses C1-C8 hydrocarbon and C1-C8 halogenated hydrocarbon.

The term "$^{18}$O-isotopically enriched oxygen" as used herein refers to molecular oxygen that is enriched with the Oxygen-18 isotope, one of the natural isotopes of oxygen. Naturally occurring oxygen is composed of three stable isotopes, Oxygen-16, Oxygen-17 and Oxygen-18, $^{16}$O being the most abundant (99.762%).

The term "target" as used herein refers to a physical object that contains the material to be irradiated with protons, and that is coupled to the cyclotron chamber where protons are accelerated. For instance, the target can be integrated by different parts, mainly: (i) a collimator to focus the proton beam; (ii) a spacer that physically separates the cyclotron main chamber from the material to be irradiated; (iii) the target body, that is directly in contact with the material to be irradiated.

The term "cryogenic retrieval" as used herein refers to a process to recover a material by cooling. For example, when irradiation of the gas in the target finishes, the pressure in the target body can be ca. 20 bar. The target body can be connected via a stainless steel tube and a valve to a stainless steel container. The stainless steel container can be cooled with liquid nitrogen and the valve can be opened. As a result, the pressure in the stainless steel container decreases. This decrease in the pressure can "suck" the irradiated gas from the target body to the stainless steel container.

The term "solid phase extraction" as used herein refers to a sample preparation process by which compounds that are in a gas mixture are separated from other compounds in the mixture according to their physical and chemical properties, using a solid trap (e.g. powder).

The term "cold cryogenic trap" as used herein refers to a container immersed in a cold bath, in the case of the present invention, liquid nitrogen, although any cooling agent could be used.

As mentioned above, the first aspect of the present invention is a process for the preparation of a pharmaceutical composition comprising an $^{18}$F-labelled gas selected from the group consisting of $^{18}$F-labelled sulphur hexafluoride ($SF_6$) and $^{18}$F-labelled carbon tetrafluoride ($CF_4$), comprising the steps: a) Filling a target with a gas mixture comprising a fluorinated gas selected from the group consisting of sulphur hexafluoride ($SF_6$) and carbon tetrafluoride ($CF_4$); b) Irradiating the gas mixture of step a) with protons with energies from 0.1 to 50 MeV;

In a particular embodiment of the first aspect of the invention, in step b) the irradiation of the gas mixture of step a) is with protons with energies from 1 to 50 MeV.

In a particular embodiment of the first aspect of the invention, in step b) the irradiation of the gas mixture of step a) is with protons with energies from 10 to 50 MeV.

In a particular embodiment of the first aspect of the invention, in step b) the irradiation of the gas mixture of step a) is with protons with energies from 10 to 40 MeV.

In a particular embodiment of the first aspect of the invention, in step b) the irradiation of the gas mixture of step a) is with protons with energies from 10 to 30 MeV.

In a particular embodiment of the first aspect of the invention, in step b) the irradiation of the gas mixture of step a) is with protons with energies from 10 to 20 MeV.

In a particular embodiment of the first aspect of the invention, the process for the preparation of the pharmaceutical composition comprises a previous step comprising: filling the target with a gas mixture comprising $^{18}$O-isotopically enriched Oxygen, irradiating the gas mixture with protons with energies in the range from 2 to 18 MeV and subsequently removing the mixture of irradiated gas comprising $^{18}$O-isotopically enriched Oxygen from the target.

In a particular embodiment of the first aspect of the invention, the process for the preparation of the pharmaceutical composition comprises a previous step comprising: filling the target with a gas mixture comprising $^{18}$O-isotopically enriched Oxygen, irradiating the gas mixture with protons with energies in the range from 3 to 10 MeV and subsequently removing the mixture of irradiated gas comprising $^{18}$O-isotopically enriched Oxygen from the target.

In a particular embodiment of the first aspect of the invention, the process for the preparation of the pharmaceutical composition comprises a previous step comprising: filling the target with a gas mixture comprising $^{18}$O-isotopically enriched Oxygen, irradiating the gas mixture with protons with energies in the range from 4 to 8 MeV and subsequently removing the mixture of irradiated gas comprising $^{18}$O-isotopically enriched Oxygen from the target.

In a particular embodiment of the first aspect of the invention, the process further comprises the steps: c) Purifying either the mixture of $^{18}$F-labelled plus unlabelled sulphur hexafluoride ($SF_6$) or the mixture of $^{18}$F-labelled plus unlabelled carbon tetrafluoride ($CF_4$); d) Formulating either the $^{18}$F-labelled plus unlabelled $SF_6$ or the $^{18}$F-labelled plus unlabelled $CF_4$ with a pharmaceutically acceptable carrier.

In a particular embodiment of the first aspect of the invention, the target is made of aluminium, nickel, niobium, silver, quartz, graphite, glass, gold, titanium, chromium, iron or a combination thereof.

In a particular embodiment of the first aspect of the invention, the gas mixture of step a) or the pharmaceutically acceptable carrier of step d) comprise air, molecular fluorine ($F_2$), nitrogen, oxygen, carbon dioxide, hydrogen, an inert gas, a sulphur fluoride, a carbon fluoride, an optionally halogenated low molecular weight hydrocarbon, or combinations thereof.

In a particular embodiment of the first aspect of the invention in step c) the purification of $^{18}$F-labelled plus unlabelled sulphur hexafluoride ($SF_6$) or the purification of $^{18}$F-labelled plus unlabelled carbon tetrafluoride ($CF_4$) is carried out by solid phase extraction and the purified gas is trapped in a cold cryogenic trap.

As it has been stated above, a second aspect of the invention is a pharmaceutical composition comprising a pharmaceutically effective amount of an $^{18}$F-labelled gas selected from the group consisting of $^{18}$F-labelled sulphur hexafluoride ($SF_6$) and $^{18}$F-labelled carbon tetrafluoride ($CF_4$), and at least one pharmaceutically acceptable carrier.

The pharmaceutical composition which is the second aspect of the invention will typically be produced in a facility endowed with a cyclotron or any other technology suitable to produce the labelled gas and will have to be transported to the site of use (typically a hospital). In order to do so, the labelled gas will have to be handled in a container suitable for the transportation of radioactive gases.

In a particular embodiment of the second aspect of the invention, the $^{18}$F-labelled gas is $^{18}$F-labelled $SF_6$ and the pharmaceutically acceptable carrier is selected from the group consisting of air, water, nitrogen, oxygen, carbon dioxide, hydrogen, an inert gas, a sulphur fluoride, a C1-C8 hydrocarbon, a C1-C8 halogenated hydrocarbon and combinations thereof.

In a particular embodiment of the second aspect of the invention, the $^{18}$F-labelled gas is $^{18}$F-labelled $CF_4$ and the pharmaceutically acceptable carrier is selected from the group consisting of air, water, nitrogen, oxygen, carbon dioxide, hydrogen, an inert gas, a sulphur fluoride, a C1-C8 hydrocarbon, a C1-C8 halogenated hydrocarbon and combinations thereof.

In a particular embodiment of the second aspect of the invention, the inert gas is selected from the group consisting of helium (He), argon (Ar), neon (Ne), krypton (Kr), xenon (Xe), and radon (Rn), N2, CO2, halogenated hydrocarbons and combinations thereof.

In a particular embodiment of the second aspect of the invention, the concentration of either $^{18}$F-labelled plus unlabelled $SF_6$ or $^{18}$F-labelled plus unlabelled $CF_4$ is from $8 \times 10^{-6}$% to 80%, expressed in volume, at P=1 bar and T=298K.

In a particular embodiment of the second aspect of the invention, the concentration of either $^{18}$F-labelled plus unlabelled $SF_6$ or $^{18}$F-labelled plus unlabelled $CF_4$ is from $8 \times 10^{-3}$% to 80%, expressed in volume, at P=1 bar and T=298K.

In a particular embodiment of the second aspect of the invention, the concentration of either $^{18}$F-labelled plus unlabelled $SF_6$ or $^{18}$F-labelled plus unlabelled $CF_4$ is from $8 \times 10^{-1}$% 80%, expressed in volume, at P=1 bar and T=298K.

In a particular embodiment of the second aspect of the invention, the concentration of either $^{18}$F-labelled plus unlabelled $SF_6$ or $^{18}$F-labelled plus unlabelled $CF_4$ is from 8% to 80%, expressed in volume, at P=1 bar and T=298K.

In a particular embodiment of the second aspect of the invention, the concentration of radioactivity due to $^{18}$F-labelled $SF_6$ or $^{18}$F-labelled $CF_4$ is from 0.3 MBq/L to 37000 MBq/L, measured at P=1 bar and T=298K.

In a particular embodiment of the second aspect of the invention, the concentration of radioactivity due to $^{18}$F-labelled $SF_6$ or $^{18}$F-labelled $CF_4$ is from 0.3 MBq/L to 247 MBq/L, measured at P=1 bar and T=298K.

In a particular embodiment of the second aspect of the invention, the total amount of either $^{18}$F-labelled plus unlabelled $SF_6$ or $^{18}$F-labelled plus unlabelled $CF_4$ administered is from 0.1 ng to 5 g per kilogram of body weight.

In a particular embodiment of the second aspect of the invention, the total amount of either $^{18}$F-labelled plus unlabelled $SF_6$ or $^{18}$F-labelled plus unlabelled $CF_4$ administered is from 0.1 ng to 100 mg per kilogram of body weight.

In a particular embodiment of the second aspect of the invention, the total amount of either $^{18}$F-labelled plus unlabelled $SF_6$ or $^{18}$F-labelled plus unlabelled $CF_4$ administered is from 0.5 ng to 50 mg per kilogram of body weight.

In a particular embodiment of the second aspect of the invention, the total amount of either $^{18}$F-labelled plus unlabelled $SF_6$ or $^{18}$F-labelled plus unlabelled $CF_4$ administered is from 0.8 ng to 20 mg per kilogram of body weight.

In a particular embodiment of the second aspect of the invention, the total amount of either $^{18}$F-labelled plus unlabelled $SF_6$ or $^{18}$F-labelled plus unlabelled $CF_4$ administered is from 1 ng to 10 mg per kilogram of body weight.

In a particular embodiment of the second aspect of the invention, the $^{18}$F-labelled gas is $^{18}$F-labelled $SF_6$, the pharmaceutically acceptable carrier is selected from the group consisting of air, water, nitrogen, oxygen, carbon dioxide, hydrogen, an inert gas, a sulphur fluoride, and optionally halogenated low molecular weight hydrocarbon and combinations thereof, and the total amount of $^{18}$F-labelled plus unlabelled $SF_6$ administered is from 0.1 ng to 100 mg per kilogram of body weight.

In a particular embodiment of the second aspect of the invention, the $^{18}$F-labelled gas is $^{18}$F-labelled $CF_4$, and the pharmaceutically acceptable carrier is selected from the group consisting of air, water, nitrogen, oxygen, carbon dioxide, hydrogen, an inert gas, a sulphur fluoride, an optionally halogenated low molecular weight hydrocarbon and combinations thereof, and the total amount of $^{18}$F-labelled plus unlabelled $CF_4$ administered is from 0.1 ng to 100 mg per kilogram of body weight In a particular embodiment of the second aspect of the invention, the $^{18}$F-labelled gas is $^{18}$F-labelled $SF_6$, the pharmaceutically acceptable carrier is selected from the group consisting of air, water, nitrogen, oxygen, carbon dioxide, hydrogen, an inert gas, a sulphur fluoride, and optionally halogenated low molecular weight hydrocarbon and combinations thereof, and the concentration of $^{18}$F-labelled plus unlabelled $SF_6$ is from $8 \times 10^{-6}$% to 80%, expressed in volume, at P=1 bar and T=298K.

In a particular embodiment of the second aspect of the invention, the $^{18}$F-labelled gas is $^{18}$F-labelled $CF_4$, and the pharmaceutically acceptable carrier is selected from the group consisting of air, water, nitrogen, oxygen, carbon dioxide, hydrogen, an inert gas, a sulphur fluoride, an optionally halogenated low molecular weight hydrocarbon and combinations thereof, and the concentration of $^{18}$F-labelled plus unlabelled $CF_4$ is from $8 \times 10^{-6}$% to 80%, expressed in volume, at P=1 bar and T=298K.

In a particular embodiment of the second aspect of the invention, the $^{18}$F-labelled gas is $^{18}$F-labelled $SF_6$, the pharmaceutically acceptable carrier is selected from the group consisting of air, water, nitrogen, oxygen, carbon dioxide, hydrogen, an inert gas, a sulphur fluoride, and optionally halogenated low molecular weight hydrocarbon and combinations thereof, and the concentration of radioactivity due to $^{18}$F-labelled $SF_6$ is from 0.3 MBq/L to 37000 MBq/L, measured at P=1 bar and T=298K.

In a particular embodiment of the second aspect of the invention, the $^{18}$F-labelled gas is $^{18}$F-labelled $CF_4$, and the pharmaceutically acceptable carrier is selected from the group consisting of air, water, nitrogen, oxygen, carbon dioxide, hydrogen, an inert gas, a sulphur fluoride, an optionally halogenated low molecular weight hydrocarbon and combinations thereof, and the the concentration of radioactivity due to $^{18}$F-labelled $CF_4$ is from 0.3 MBq/L to 37000 MBq/L, measured at P=1 bar and T=298K.

It also forms part of the invention a pharmaceutical composition according to the second aspect of the invention obtainable by the process of the first aspect of the invention.

As it has been stated above, a third aspect of the invention is the pharmaceutical composition according to the second aspect of the invention for use as an image contrast agent. This third aspect can be also formulated as a pharmaceutical composition according to the second aspect of the invention for use in the assessment of lung function, and additionally as a pharmaceutical composition according to the second aspect of the invention for use in diagnosis, prognosis and stratification of pulmonary disease.

The third aspect of the invention can also be formulated as the use of an $^{18}$F-labelled gas selected from the group consisting of $^{18}$F-labelled $SF_6$ and $^{18}$F-labelled $CF_4$ for the preparation of a pharmaceutical composition for the assessment of lung function. The third aspect of the invention can also be formulated as the use of an $^{18}$F-labelled gas selected from the group consisting of $^{18}$F-labelled $SF_6$ and $^{18}$F-labelled $CF_4$ for the preparation of a pharmaceutical composition for the diagnosis, prognosis and stratification of respiratory disease.

The third aspect can also be formulated as a method for the assessment of lung function which comprises administering a pharmaceutically effective amount of an $^{18}$F-labelled gas selected from the group consisting of $^{18}$F-labelled $SF_6$ and $^{18}$F-labelled $CF_4$ to a subject in need thereof, including a human. The third aspect can also be formulated as a method of diagnosis, prognosis and stratification of respiratory disease which comprises administering a pharmaceutically effective amount of an $^{18}$F-labelled gas selected from the group consisting of $^{18}$F-labelled $SF_6$ and $^{18}$F-labelled $CF_4$ to a subject in need thereof, including a human.

In a particular embodiment of the third aspect of the invention, the use as an image contrast agent is in the study of respiratory disease, wherein the respiratory disease is selected from the group consisting of asthma, cystic fibrosis, lung cancer, emphysema, chronic obstructive pulmonary disease (COPD), chronic bronchitis, pulmonary fibrosis, tuberculosis, chronic respiratory failure and acute respiratory distress syndrome.

In a particular embodiment of the third aspect of the invention, the imaging is carried out by Positron Emission Tomography (PET).

In a particular embodiment of the third aspect of the invention, the respiratory disease is selected from the group consisting of asthma, cystic fibrosis, lung cancer, emphysema, chronic obstructive pulmonary disease (COPD), chronic bronchitis, pulmonary fibrosis, tuberculosis, chronic respiratory failure and acute respiratory distress syndrome, and the imaging is carried out by Positron Emission Tomography (PET).

It is understood herein that a "respiratory disease" is a disease that impairs proper lung function, either by having its origin in the respiratory tract or because the disease has its origin in another system or organ but affects the respiratory tract as a side-effect.

Throughout the description and claims the word "comprise" and variations of the word, are not intended to exclude other technical features, additives, components, or steps.

Furthermore, the word "comprise" and its variations encompasses the term "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

A) Material and Methods
Production of [$^{18}$F]$CF_4$ and [$^{18}$F]$SF_6$
Target Configuration:

The strategy for the production of [$^{18}$F]$CF_4$ and [$^{18}$F]$SF_6$ is based in the double shoot method using the target provided by IBA (http://www.iba-radiopharmasolutions.com) for the production of [$^{18}$F]$F_2$ (see FIG. 1 for scheme).

The target consists of an aluminum target body (internal volume around 50 mL) physically isolated from the cyclotron main chamber by two metallic disks (made of aluminum and titanium) both cooled with helium gas. The target body and the collimator are water cooled. The target chamber (2 in FIG. 1) contains the gas that is irradiated with the protons (1 in FIG. 1). The target chamber has two inlet/outlet ports connected via stainless steel tubing to remotely-controlled electro-valves ($V_1$-$V_6$ in FIG. 1). $V_1$ is connected to a stainless steel-high pressure container (3 in FIG. 1) which can be introduced in a liquid nitrogen cooling bath. $V_2$ is connected to the radiochemistry lab (outside the cyclotron vault, 8 in FIG. 1). $V_3$ is an exhaust (4 in FIG. 1). $V_4$ is connected to the [$^{18}$O]$O_2$ gas bottle (5 in FIG. 1). $V_5$ and $V_6$ are connected to the Neon and $CF_4$/$SF_6$ bottles, respectively, both of them placed out of the cyclotron vault (6 and 7 in FIG. 1, respectively).

Production Process A:

Step 1: The target was filled with [$^{18}$O]$O_2$ by opening $V_4$ to a final pressure $P_1$. After reaching the appropriate pressure, $V_4$ was closed.

Step 2: The target was irradiated with protons (nominal energy of the cyclotron=18 MeV) at a proton intensity of 15 pA measured in the target and an integrated current of $C_1$ µAh.

Step 3: After irradiation, the stainless steel-high pressure container was introduced in the liquid nitrogen bath, $V_1$ was opened and the gas content of the target was recovered in the container. When the pressure in the target was below 0.2 bar (absolute pressure), $V_1$ was closed.

Step 4: $V_6$ was opened and the target chamber was filled with $CF_4$ or $SF_6$ gas (for the production of [$^{18}$]$CF_4$ or [$^{18}$F]$SF_6$, respectively) to a pressure $P_2$. After reaching the appropriate pressure, $V_6$ was closed.

Step 5: $V_5$ was opened and the target chamber was topped with Neon gas to a final pressure $P_3$. After reaching the appropriate pressure, $V_5$ was closed.

Step 6: The target was irradiated with protons at a proton intensity of 15 pA measured in the target and an integrated current of $C_2$ pAh.

Figure 2:
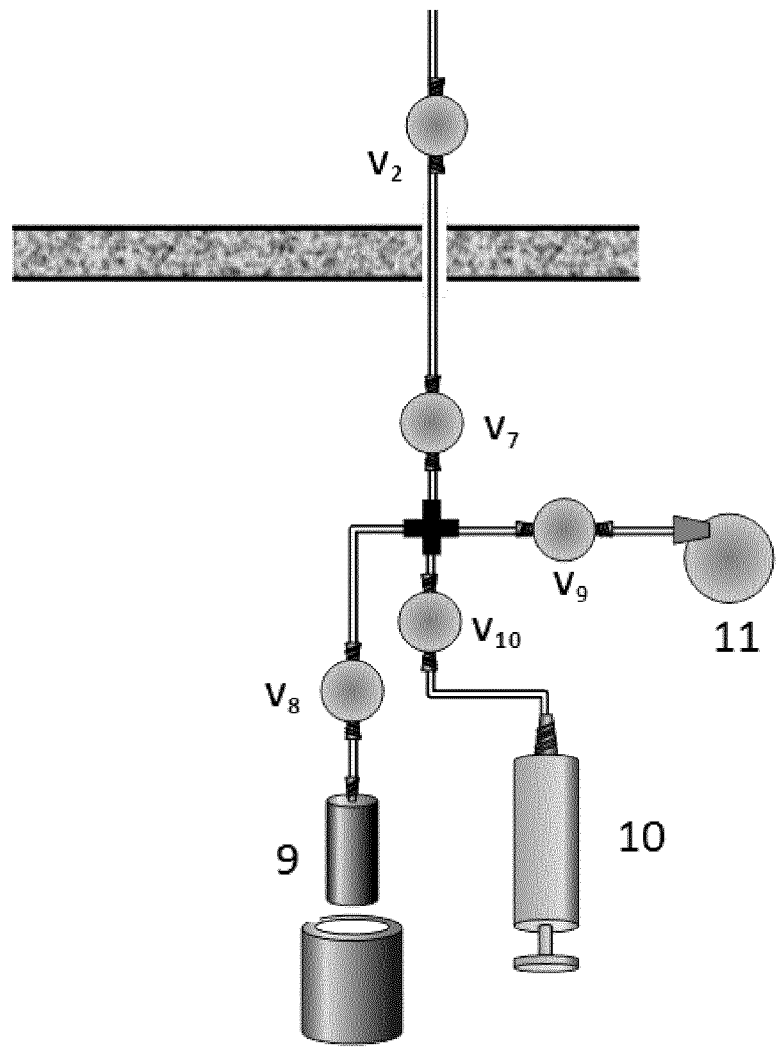
FIG. 2. Configuration of the collection system placed into one of the hot cells of the radiochemistry lab: (9) stainless steel-high pressure container and liquid nitrogen cooling bath; (10) gas-tight syringe; (11) vacuum pump; $V_2$ is the same valve as in FIG. 1; $V_7$-$V_{10}$ are 2-way, normally-closed electro-valves.

Step 7: After the end of the second irradiation, $V_2$, $V_7$, and $V_8$ were opened and the target gas was unloaded to one of the hot cells in the radiochemistry lab into a stainless steel-high pressure container immersed in a liquid nitrogen cooling bath (9 in FIG. 2). NOTE: Previous to the transfer of the activity to the radiochemistry lab, the stainless steel-high pressure container was emptied under vacuum by opening $V_8$ and $V_9$ (FIG. 2).

Step 8: After complete transfer (pressure in the target<1 bar above atmospheric pressure) $V_2$, $V_7$, and $V_8$ were closed and after 120 minutes, the activity present in the stainless steel-high pressure container was measured in a dose calibrator.

Step 9: A fraction of the gas was collected in a gas-tight syringe (10 in FIG. 2) by opening $V_8$ and $V_{10}$, and the sample was analyzed as explained below.

Production Process B:

Because $^{19}F$ is known to undergo the $^{19}F(p, pn)^{18}F$ nuclear reaction, we explored the formation of $[^{18}F]CF_4$ and $[^{18}F]SF_6$ by direct irradiation of mixtures of $CF_4$/Neon or $SF_6$/Neon, respectively, in a single shot method. The process was as follows:

Step 1: $V_6$ in FIG. 1 was opened and the target chamber was filled with $CF_4$ or $SF_6$ gas to a pressure $P_2$. After reaching the appropriate pressure, $V_6$ was closed.

Step 2: $V_5$ in FIG. 1 was opened and the target chamber was topped with Neon gas to a final pressure $P_3$. After reaching the appropriate pressure, $V_5$ was closed.

Step 3: The target was irradiated with protons at a proton intensity of 15 µA measured in the target and an integrated current of $C_2$ µAh.

Step 4: After the end of the irradiation, $V_2$, $V_7$, and $V_8$ were opened and the target gas was unloaded to one of the hot cells in the radiochemistry lab into a stainless steel-high pressure container immersed in a liquid nitrogen cooling bath (9 in FIG. 2). NOTE:

Previous to the transfer of the activity to the radiochemistry lab, the stainless steel-high pressure container was emptied under vacuum by opening $V_8$ and $V_9$ (FIG. 2).

Analysis of the Trapped Gas (for both Methods):

A fraction of the trapped gas was analysed by gas-chromatography-Mass spectrometry, immediately after transfer and at t=120 minutes. Analyses were performed on an Agilent 7820A network GC connected to an Agilent 5975c inert XL MSD with Triple axis detector and a radioactivity detector. A J&W PoraPlot column (length: 27.5 m, internal diameter: 0.32 mm) was used as stationary phase. The inlet conditions were 150° C., 6.8 psi and a flow rate of 2.5 ml/min. Helium (99.9999%) was used as the carrier gas. The oven temperature was set to 36° C. The analyses were made in scan mode.

Imaging Studies

Imaging studies were conducted with $[^{18}F]CF_4$.

Animals:

Male rats (n=2) weighing 350±14 g (Sprague-Dawley, Harlan, Udine, Italy) were used to perform PET studies. The animals were cared for and handled in accordance with the Guidelines for Accommodation and Care of Animals (European Convention for the Protection of Vertebrate Animals Used for Experimental and Other Scientific Purposes) and internal guidelines, and experimental procedures were approved by the Ethical Committee and local authorities.

Figure 3:
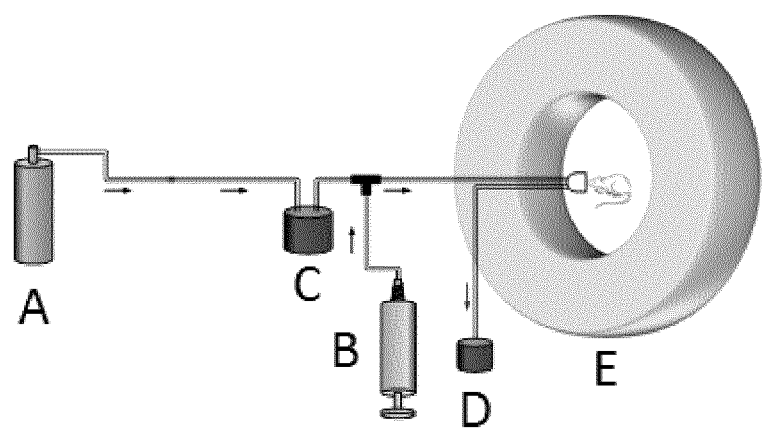
FIG. 3. Configuration of the administration system. The mixture [$^{18}$F]CF$_4$/CF$_4$/Ne is introduced in a gas-tight syringe (B) placed in an automated syringe pump, and released at 10 mL/min into the main oxygen gas stream just after the isofluorane vaporizer (C). The oxygen is obtained from a gas bottle (A) at a flow of 1 L/min. The animal, placed into the PET-CT camera (E) inhales the radioactive gas mixed with the oxygen (carrier) and the isofluorane. The exhaust gas is passed through an active charcoal filter.

Administration of the Labelled Compounds:

The radioactive gas was administered by inhalation, by mixing the mixture $[^{18}F]CF_4/CF_4$/Ne obtained at the end of the production process (process A) with the oxygen carrier gas. With that aim, the system depicted in FIG. 3 was implemented.

PET-CT System:

PET studies were performed using an eXploreVista-CT small animal PET-CT system (GE Healthcare).

Image Acquisition:

The procedure was as follows:

Step 1: Rats were anesthetized in an induction chamber using a mixture of 3-4% isoflurane in $O_2$.

Step 2: Animals were rapidly moved into the PET-CT camera, were anaesthesia was maintained with a mixture of 1.5-2.0% isoflurane in $O_2$. During the stay into the PET-CT camera, animals were kept normothermic using a heating blanket (Homeothermic Blanket Control Unit; Bruker). Regular breathing (frequency of 50±10 breaths/minute) was maintained by adjustment of anaesthetic conditions. Respiration and body temperature of the animals were monitored throughout the scan.

Step 3: At t=0 min, with the animal under anaesthesia, acquisition of PET images was started in list mode.

Step 4: At t=1 minute, the syringe pump was started and the radioactive gas ($[^{18}F]CF_4$, diluted with Neon and non-radioactive $CF_4$, 74 MBq, 2 mCi) was introduced in the main stream of oxygen and consequently administered to the animal.

Step 5: At t=2 minutes, the syringe pump was stopped, and image acquisition was continued until t=10 minutes.

Step 6: After finalising the PET image acquisition, a whole body CT scan was performed, providing anatomical information as well as the attenuation map, for the later image reconstruction.

Image Reconstruction and Analysis:

Images were reconstructed (decay and CT-based attenuation corrected) with OSEM-2D. Twenty nine frames (3×20s, 10×10s, 4×20s and 12×30s) were defined to gain information about the spatiotemporal distribution of the radioactivity. PET images were analysed using PMOD image analysis software (PMOD Technologies Ltd, Zurich, Switzerland). Volumes of interest (VOIs) were manually drawn in the lungs on the CT images. VOIs were then transferred to the PET images and the concentration of radioactivity was obtained for each organ and time frame as cps/cm$^3$. All frames were finally summed and re-processed to get more accurate images of the distribution of radioactivity within the lungs.

B) Results

Production of $[^{18}F]CF_4$

Production Process A: Identification of the Radioactive and Non-Radioactive Gases:

Initial experiments were performed by fixing the following experimental conditions: $P_1$=20 bar; $C_1$=1 pAh; $P_2$=4 bar; $P_3$=20 bar; $C_2$=1 pAh. These experiments were conducted to identify the radioactive and non radioactive gases present in the final gas collected in the radiochemistry lab.

Figure 4:
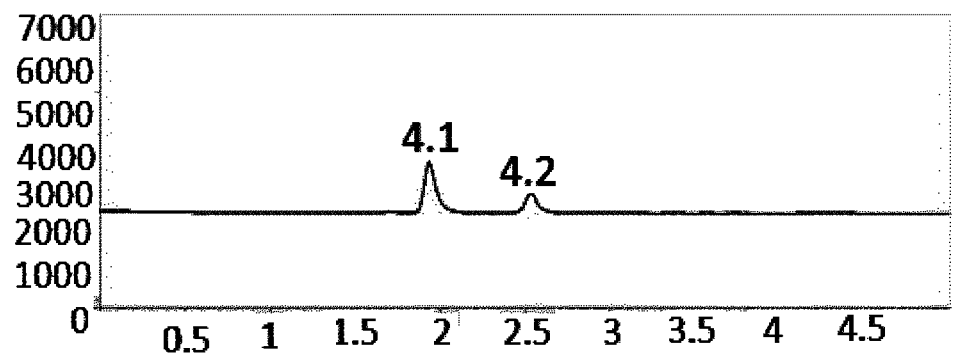
FIG. 4. Chromatogram (radioactivity detector) corresponding to the analysis of cyclotron produced [$^{18}$F]CF$_4$ immediately after transfer of the activity to the radiochemistry lab. Two radioactive peaks, with retention times of 1.93 (4.1) and 2.53 min (4.2), respectively, corresponding to [$^{18}$F]CF$_4$ (4.1) and [$^{11}$C]CO$_2$ (4.2), are identified.
Figure 5:
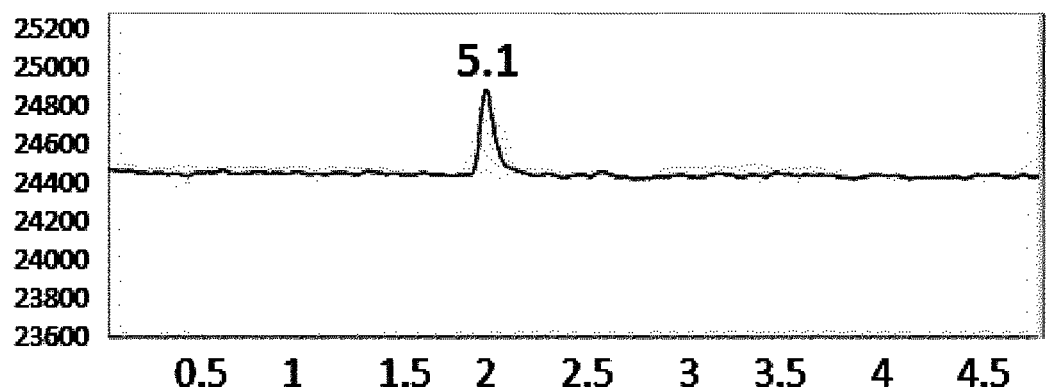
FIG. 5. Chromatogram (radioactivity detector) corresponding to the analysis of cyclotron produced [$^{18}$F]CF$_4$ 120 minutes after transfer of the activity to the radiochemistry lab. Only one radioactive peak, with retention time of 1.93 min (5.1), corresponding to [$^{18}$F]CF$_4$ can be identified.
Figure 6:
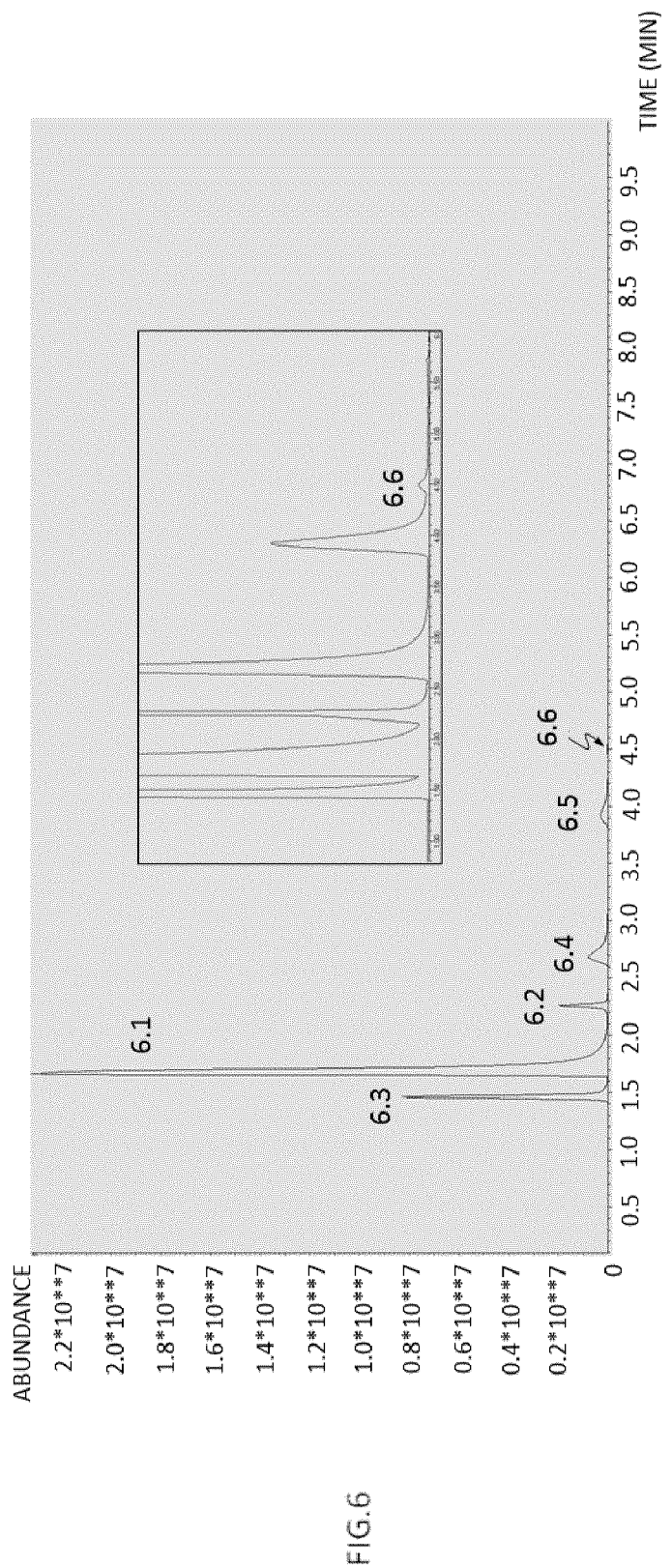
FIG. 6. Chromatogram (MS detector) corresponding to the analysis of cyclotron produced [$^{18}$F]CF$_4$ after transfer of the activity to the radiochemistry lab. Five major species with retention times=1.45, 1.65, 2.25, 2.70 and 3.92, that were identified with the mass spectra as N$_2$ (6.3), CF$_4$ (6.1), CO$_2$ (6.2), C$_2$F$_6$ (6.4), and C$_2$F$_6$O$_3$ (6.5), respectively, were observed. One very minor peak appeared at RT=4.50 min, but the chemical structure could not be elucidated (6.6, insert).

GC-MS analysis performed just after irradiation confirmed the presence of two radioactive gases, with retention times (RTs) of 1.93 and 2.53 min, corresponding to $[^{18}F]CF_4$ and $[^{11}C]CO_2$ by co-elution with reference standards (FIG. 4). Analysis of the same sample after 120 min confirmed the complete disappearance of the peak corresponding to $[^{11}C]CO_2$ (FIG. 5). MS analysis confirmed the presence of 5 major species with RTs=1.45, 1.65, 2.25, 2.70 and 3.92, that were identified with the mass spectra as $N_2$, $CF_4$, $CO_2$, $C_2F_6$, and $C_2F_6O_3$, respectively (FIG. 6). One very minor peak appeared at RT=4.50 min, but the chemical structure could not be elucidated (FIG. 6, insert).

Production Process A: Formation of $[^{18}F]CF_4$:

After identification of the radioactive and non radioactive gases present in the final mixture, experiments were performed by fixing the following experimental conditions: $P_1$=20 bar; $C_1$=1 or 4 pAh; $P_2$=4 bar; $P_3$=20 bar; $C_2$=1, 2 or 4 µAh. After the second irradiation and trapping of the irradiated gas in the stainless steel-high pressure container, $V_8$ was closed. After 120 minutes, the amount of activity was measured in a dose calibrator and the gas was analyzed using the same analytical system as described above. The results expressed as amount of radioactivity, decay corrected to the end of the irradiation process, are shown in Table 1.

TABLE 1

Amount of activity, decay corrected to the end of irradiation, obtained under different experimental conditions for production process A.

| Entry | $C_1$ (μAh) | $C_2$ (μAh) | Mean (GBq) | SDEV (GBq) |
|---|---|---|---|---|
| 1 | 1 | 1 | 2.30 | 0.08 |
| 2 | 1 | 2 | 2.47 | 0.08 |
| 3 | 1 | 4 | 2.75 | 0.13 |
| 4 | 4 | 4 | 8.43 | 0.59 |

As it can be seen in the table, the amount of activity generated was quite independent of $C_2$ value, suggesting that the isotopic exchange reaction is relatively fast. Increasing the integrated current $C_1$ resulted in a significant increase in the final amount of radioactivity, as shown in entry 4.

Production Process B: Identification of the Radioactive and Non-Radioactive Gases Chromatographic profiles equivalent to those obtained when method A was used were obtained.

Production Process B: Formation of $[^{18}F]CF_4$:

Experiments were performed by fixing the following experimental conditions: $P_2$=2 or 4 bar; $P_3$=20 bar; $C_2$=4 or 8 pAh. After the irradiation and trapping of the irradiated gas in the stainless steel-high pressure container, $V_8$ was closed. After 120 minutes, the amount of activity was measured in a dose calibrator and the gas was analyzed using the same analytical system as described above. The results expressed as amount of radioactivity, decay corrected to the end of the irradiation process, are shown in Table 2.

TABLE 2

Amount of activity, decay corrected to the end of irradiation, obtained under different experimental conditions for production process B.

| Entry | $P_2$ (bar) | $C_2$ (μAh) | Mean (GBq) | SDEV (GBq) |
|---|---|---|---|---|
| 1 | 2 | 4 | 0.27 | 0.03 |
| 2 | 2 | 8 | 0.49 | 0.04 |
| 3 | 4 | 4 | 0.58 | 0.04 |
| 4 | 4 | 8 | 0.80 | 0.06 |

As it can be seen, despite the presence of $[^{18}F]CF_4$ could be detected, the production yield was much lower than that obtained using the double shot method. For equivalent experimental conditions ($P_2$=4 bar; $C_2$=4 pAh, entries 4 in Table 1 and 3 in Table 2), values of 8.43±0.59 and 0.58±0.04 were obtained for methods A and B, respectively.

Production of $[^{18}F]SF_6$

Figure 7:
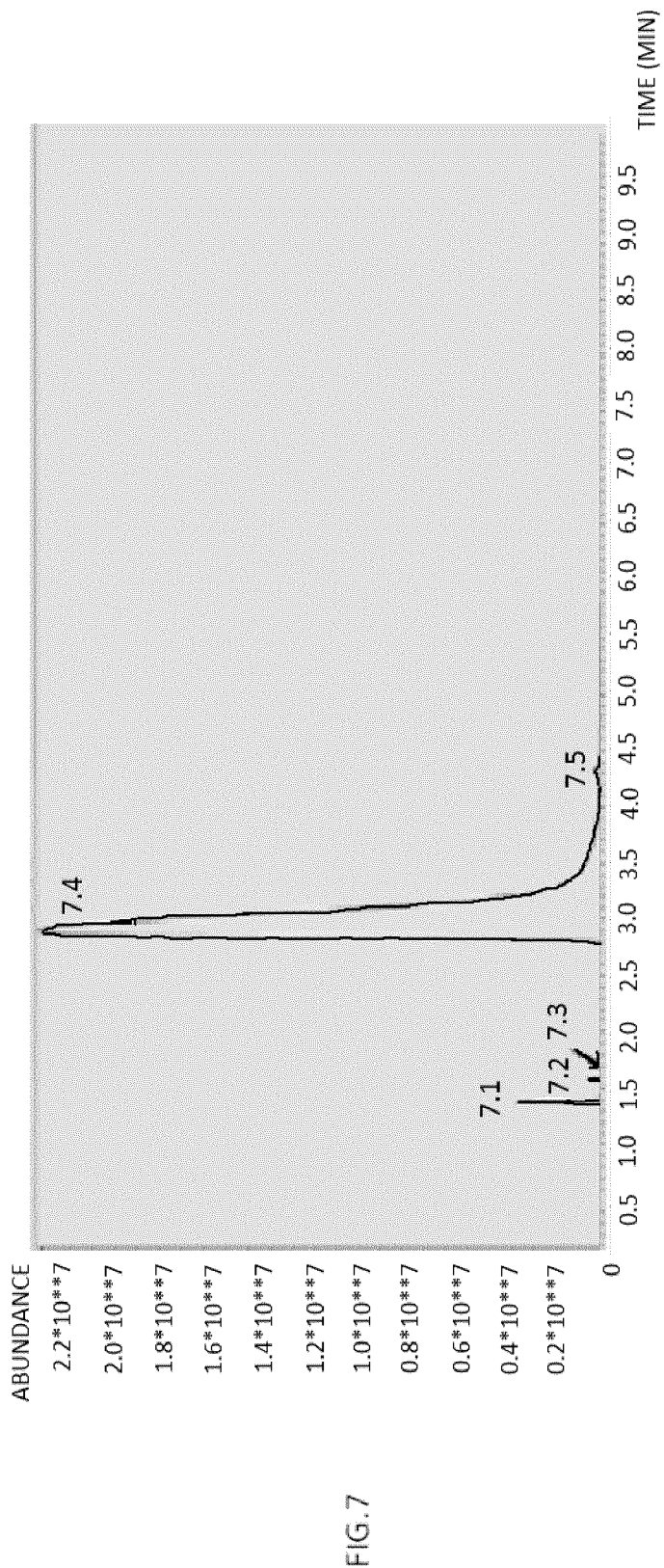
FIG. 7. Chromatogram (MS detector) corresponding to the analysis of cyclotron produced [$^{18}$F]SF$_6$ after transfer of the activity to the radiochemistry lab. Four major species with retention times=1.45, 1.65, 1.70 and 2.95 were identified with the mass spectra as N$_2$ (7.1), CF$_4$ (7.2), F$_3$N (7.3), and SF$_6$ (7.4). One unidentified peak was found at RT=4.35 (7.5).

Production Process A: Identification of the Radioactive and Non-Radioactive Gases For the production of this radioactive species, only optimal experimental conditions were assayed: $P_1$=20 bar; $C_1$=4 pAh; $P_2$=4 bar; $P_3$=20 bar; $C_2$=4 pAh. The analysis of the radioactive gas by radio GC-MS confirmed, after 120 min of decay, the presence of only one radioactive species with RT=3.35 min, which was identified as $[^{18}F]SF_6$. MS analysis confirmed the presence of 5 species with RTs=1.45, 1.65, 1.70, 2.95 and 4.35, that were identified with the mass spectra as $N_2$, $CF_4$, $F_3N$, $SF_6$, and one unidentified compound (FIG. 7).

Production process A: Formation of $[^{18}F]SF_6$:

The results expressed as amount of radioactivity, decay corrected to the end of the irradiation process, are shown in Table 3.

TABLE 3

Amount of activity, decay corrected to the end of irradiation, obtained for production process A.

| Entry | $C_1$ (μAh) | $C_2$ (μAh) | Mean (GBq) | SDEV (GBq) |
|---|---|---|---|---|
| 1 | 4 | 4 | 6.77 | 0.21 |

Production Process B: Identification of the Radioactive and Non-Radioactive Gases Chromatographic profiles equivalent to those obtained when method A was used were obtained.

Production Process B: Formation of $[^{18}F]SF_6$:

Experiments were performed by fixing the following experimental conditions: $P_2$=4 bar; $P_3$=20 bar; $C_2$=4 pAh. After the irradiation and trapping of the irradiated gas in the stainless steel-high pressure container, $V_8$ was closed. After 120 minutes, the amount of activity was measured in a dose calibrator and the gas was analyzed using the same analytical system as described above. The results expressed as amount of radioactivity, decay corrected to the end of the irradiation process, are shown in Table 4.

TABLE 4

Amount of activity, decay corrected to the end of irradiation, obtained for production process B.

| Entry | $P_2$ (bar) | $C_2$ (μAh) | Mean (GBq) | SDEV (GBq) |
|---|---|---|---|---|
| 1 | 4 | 4 | 0.36 | 0.05 |

As it can be seen, despite the presence of $[^{18}F]SF_6$ could be detected, the production yield was much lower than that obtained using the double shot method.

Imaging Studies

Figure 8:
FIG. 8. PET-CT images showing the distribution of the radioactive gas in the lungs. Images are the result of summing all reconstructed frames: (A) 3D-volume render of the CT and the PET image, in sagital (left) and coronal (right) views; the lungs are marked as 8.1; (B) representative coronal slices; the lungs are marked as 8.2.
Figure 9:
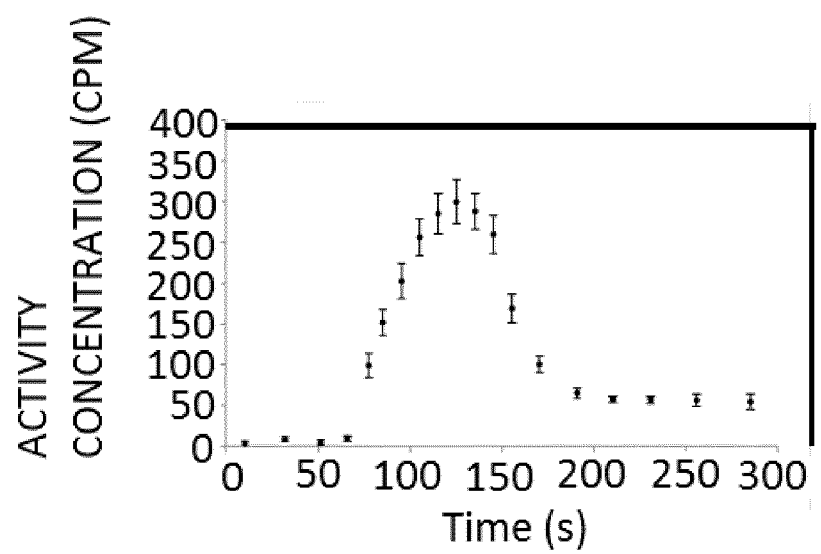
FIG. 9. Concentration of radioactivity in the lungs as a function of time, as calculated from PET-CT images. Results are mean±standard deviation, n=2.

Summed images clearly show a uniform distribution of the radioactive gas in the lungs (FIG. 8). Dynamic images showed immediate distribution of the radioactive gas in the lungs. The time-activity curve (FIG. 9) corresponding to a VOI drawn in the whole lungs shows a plateau, which is reached immediately after the onset of contrast agent administration. When the delivery of the radioactive gas is discontinued, almost complete elimination of the radioactivity is achieved in a few seconds.

REFERENCES CITED IN THE APPLICATION

Banister S., et al., "Fluorine-18 chemistry for PET: A concise Introduction", Current Radiopharmaceuticals 2010, vol. 3, pp. 68-80

Murata K., et al. "Ventilation imaging with positron emission tomography and Nitrogen-13" Radiology 1986, vol. 158, pp. 303-307

Yu J, et al. "19F: A versatile reporter for non-invasive physiology and pharmacology using magnetic resonance" Current Medicinal Chemistry 2005, vol. 12, pp. 819-848

Gens T. A. et al. "The exchange of F18 between metallic fluorides and gaseous fluorine compounds" J. Am. Chem. Soc. 1957, vol. 79, pp. 1001-1002

Rogers M. T., Katz J. "Fluorine Exchange reactions between hydrogen fluoride and the halogen fluorides" J. Am. Chem. Soc. 1952, vol. 74, pp. 1375-1377

Boggs et al: "Non-exchange of F18 between HF and Fluorinated Methanes", J. Am. Chem. Soc., 1955, 77 (24), pp 6505-6506

Cramer et al: "Gas phase fluorination of benzene, fluorobenzene, m-difluorobenzene, and trifluoromethylbenzene by reactions of thermal fluorine-18 atoms", J. Am. Chem. Soc., 1974, 96 (21), pp 6579-6584

For reasons of completeness, various aspects of the invention are set out in the following numbered clauses:

Clause 1. A process for the preparation of a pharmaceutical composition comprising an $^{18}$F-labelled gas selected from the group consisting of $^{18}$F-labelled sulphur hexafluoride ($SF_6$) and $^{18}$F-labelled carbon tetrafluoride ($CF_4$), comprising the steps:
  a) Filling a target with a gas mixture comprising a fluorinated gas selected from the group consisting of sulphur hexafluoride ($SF_6$) and carbon tetrafluoride ($CF_4$);
  b) Irradiating the gas mixture of step a) with protons with energies from 0.1 to 50 MeV.

Clause 2. The process for the preparation of the pharmaceutical composition of clause 1, comprising a previous step comprising: filling the target with a gas mixture comprising $^{18}$F-isotopically enriched Oxygen, irradiating the gas mixture with protons with energies in the range from 2 to 18 MeV and subsequently removing the mixture of irradiated gas comprising $^{18}$O-isotopically enriched Oxygen from the target.

Clause 3. The process of any one of clauses 1-2, further comprising the steps:
  c) Purifying either the mixture of $^{18}$F-labelled plus unlabelled sulphur hexafluoride ($SF_6$) or the mixture of $^{18}$F-labelled plus unlabelled carbon tetrafluoride ($CF_4$);
  d) Formulating either the $^{18}$F-labelled plus unlabelled $SF_6$ or the $^{18}$F-labelled plus unlabelled $CF_4$ with a pharmaceutically acceptable carrier.

Clause 4. The process of any one of clauses 1-3, wherein the target is made of aluminium, nickel, niobium, silver, quartz, graphite, glass, gold, titanium, chromium, iron or a combination thereof.

Clause 5. The process for the preparation of the pharmaceutical composition of any one of clauses 1-4, wherein the gas mixture of step a) or the pharmaceutically acceptable carrier of step d) comprise air, molecular fluorine ($F_2$), nitrogen, oxygen, carbon dioxide, hydrogen, an inert gas, a sulphur fluoride, a carbon fluoride, an optionally halogenated low molecular weight hydrocarbon, or combinations thereof.

Clause 6. The process for the preparation of the pharmaceutical composition according to any one of clauses 1-5, wherein in step c) the purification of $^{18}$F-labelled plus unlabelled sulphur hexafluoride ($SF_6$) or the purification of $^{18}$F-labelled plus unlabelled carbon tetrafluoride ($CF_4$) is carried out by solid phase extraction and the purified gas is trapped in a cold cryogenic trap.

Clause 7. A pharmaceutical composition comprising a pharmaceutically effective amount of an $^{18}$F-labelled gas selected from the group consisting of $^{18}$F-labelled sulphur hexafluoride ($SF_6$) and $^{18}$F-labelled carbon tetrafluoride ($CF_4$), and at least one pharmaceutically acceptable carrier.

8. The pharmaceutical composition of clause 7 wherein the $^{18}$F-labelled gas is $^{18}$F-labelled $SF_6$ and the pharmaceutically acceptable carrier is selected from the group consisting of air, water, nitrogen, oxygen, carbon dioxide, hydrogen, an inert gas, a sulphur fluoride, a C1-C8 hydrocarbon, a C1-C8 halogenated hydrocarbon and combinations thereof.

Clause 9. The pharmaceutical composition of clause 7 wherein the $^{18}$F-labelled gas is $^{18}$F-labelled $CF_4$ and the pharmaceutically acceptable carrier is selected from the group consisting of air, water, nitrogen, oxygen, carbon dioxide, hydrogen, an inert gas, a sulphur fluoride, a C1-C8 hydrocarbon, a C1-C8 halogenated hydrocarbon and combinations thereof.

Clause 10. The pharmaceutical composition of any one of clauses 7-9, wherein the concentration of either $^{18}$F-labelled plus unlabelled $SF_6$ or $^{18}$F-labelled plus unlabelled $CF_4$ is from $8\times10^{-6}$% to 80%, expressed in volume, at P=1 bar and T=298K.

Clause 11. The pharmaceutical composition of any one of clauses 7-10, wherein the concentration of radioactivity due to $^{18}$F-labelled $SF_6$ or $^{18}$F-labelled $CF_4$ is from 0.3 MBq/L to 37000 MBq/L, measured at P=1 bar and T=298K.

Clause 12. The pharmaceutical composition of clause 11, wherein the concentration of radioactivity due to $^{18}$F-labelled $SF_6$ or $^{18}$F-labelled $CF_4$ is from 0.3 MBq/L to 247 MBq/L, measured at P=1 bar and T=298K.

Clause 13. The pharmaceutical composition according to any one of clauses 7-12 obtainable by the process as defined in any one of clauses 1-6.

Clause 14. A pharmaceutical composition as defined in any one of clauses 7-12 for use as an image contrast agent.

Clause 15. The pharmaceutical composition for use according to clause 14, wherein the imaging is carried out by Positron Emission Tomography (PET).

The invention claimed is:

1. A process for the preparation of a pharmaceutical composition comprising an $^{18}$F-labeled gas selected from the group consisting of $^{18}$F-labeled sulfur hexafluoride ($SF_6$) and $^{18}$F-labeled carbon tetrafluoride ($CF_4$), comprising the steps:
  a) Filling a target with a gas mixture comprising a fluorinated gas selected from the group consisting of sulfur hexafluoride ($SF_6$) and carbon tetrafluoride ($CF_4$);
  b) Irradiating the gas mixture of step a) with protons with energies from 0.1 to 50 MeV.

2. The process according to claim 1, comprising a previous step comprising: filling the target with a gas mixture comprising $^{18}$O-isotopically enriched Oxygen, irradiating the gas mixture with protons with energies in the range from 2 to 18 MeV and subsequently removing the mixture of irradiated gas comprising $^{18}$O-isotopically enriched Oxygen from the target.

3. The process according to claim 1, further comprising the steps:
  c) Purifying either the mixture of $^{18}$F-labeled plus unlabeled sulfur-hexafluoride ($SF_6$) or the mixture of $^{18}$F-labeled plus unlabeled carbon tetrafluoride ($CF_4$);
  d) Formulating either the $^{18}$F-labeled plus unlabeled $SF_6$ or the $^{18}$F-labeled plus unlabeled $CF_4$ with a pharmaceutically acceptable carrier.

4. The process according to claim 1, wherein the target is made of aluminium, nickel, niobium, silver, quartz, graphite, glass, gold, titanium, chromium, iron or a combination thereof.

5. The process according to claim 1, wherein the gas mixture of step a) comprises air, molecular fluorine ($F_2$), nitrogen, oxygen, carbon dioxide, hydrogen, an inert gas, a sulfur fluoride, a carbon fluoride, an optionally halogenated low molecular weight hydrocarbon, or combinations thereof.

6. The process according to claim 3, wherein in step c) the purification of $^{18}$F-labeled plus unlabeled sulfur hexafluoride ($SF_6$) or the purification of $^{18}$F-labeled plus unlabeled carbon tetrafluoride ($CF_4$) is carried out by solid phase extraction and the purified gas is trapped in a cold cryogenic trap.

7. The process according to claim 2, further comprising the steps:
- c) Purifying either the mixture of $^{18}$F-labeled plus unlabeled sulfur hexafluoride ($SF_6$) or the mixture of $^{18}$F-labeled plus unlabeled carbon tetrafluoride ($CF_4$);
- d) Formulating either the $^{18}$F-labeled plus unlabeled $SF_6$ or the $^{18}$F-labeled plus unlabeled $CF_4$ with a pharmaceutically acceptable carrier.

8. The process according to claim 2, wherein the gas mixture of step a) comprises air, molecular fluorine ($F_2$), nitrogen, oxygen, carbon dioxide, hydrogen, an inert gas, a sulfur fluoride, a carbon fluoride, an optionally halogenated low molecular weight hydrocarbon, or combinations thereof.

* * * * *